United States Patent [19]

Takahashi

[11] 4,344,918

[45] Aug. 17, 1982

[54] DETERMINATION OF TOTAL CARBON IN LIQUID SAMPLES

[75] Inventor: Yoshihiro Takahashi, San Jose, Calif.

[73] Assignee: Xertex Corporation, Menlo Park, Calif.

[21] Appl. No.: 127,333

[22] Filed: Mar. 5, 1980

[51] Int. Cl.³ .................. G01N 31/12; G01N 21/63
[52] U.S. Cl. .................................. 422/80; 250/435; 422/64; 422/81; 422/78; 23/230 PC
[58] Field of Search .................... 422/78-82, 422/64; 250/432, 435, 437, 527; 23/230 PC

[56] References Cited

U.S. PATENT DOCUMENTS

| | | | |
|---|---|---|---|
| 2,003,303 | 6/1935 | Mitscherling | 422/186 |
| 2,248,618 | 7/1941 | Fischer | 250/437 |
| 3,659,096 | 4/1972 | Kompanek | 422/24 |
| 3,854,877 | 12/1974 | Csaky et al. | 23/230 PC |
| 3,958,941 | 5/1976 | Regan | 422/80 |
| 4,013,413 | 3/1977 | Stewart et al. | 422/64 |
| 4,155,978 | 5/1979 | Naono et al. | 422/64 |

OTHER PUBLICATIONS

Goulden et al., Anal. Chem. vol. 47, No. 12, Oct. 1975, pp. 1943-1946, Automated Det. of Dissolved Organic Carbon in Lake Water.
Takahashi, Ultra Low Level TOC Analysis of Potable Waters, 1976.

Primary Examiner—Michael S. Marcus
Attorney, Agent, or Firm—Flehr, Hohbach, Test, Albritton & Herbert

[57] ABSTRACT

An apparatus for determining total carbon in each one of a plurality of discrete liquid samples comprises a reactor (13), and a pump (12) and flowline (11) for maintaining a continuous flow of a liquid containing an oxidizing agent into the reactor (13). The liquid samples are introduced in succession into the reactor (13), either by means of a syringe injection port (19) in the flowline (11), or by means of a rotary valve (203) and sample loop (204) in a recirculation line (202) through which carbon-free liquid is withdrawn from and circulated back to the reactor (13). A mercury vapor lamp (17) is immersed in the liquid in the reactor (13) for irradiating the liquid sample and the oxidizing agent in the reactor (13) with ultraviolet energy in order to oxidize to carbon dioxide any carbonaceous matter in the liquid sample. A sparger (20) is provided to remove the carbon dioxide so produced from the reactor (13); and a carbon dioxide detector (24) is provided to measure the carbon dioxide produced as a result of the oxidation of carbonaceous matter in the reactor (13). Electronic integrator circuitry (25) provides a measure of total carbon present in the carbon dioxide produced in the time interval during which carbonaceous matter in each liquid sample is being oxidized.

5 Claims, 3 Drawing Figures

DETERMINATION OF TOTAL CARBON IN LIQUID SAMPLES

BACKGROUND OF THE INVENTION

1. Field of the Invention

This invention pertains to the determination of total carbon in liquid samples.

2. State of the Prior Art

In an article by M. Ehrhardt entitled "A New Method for the Automatic Measurement of Dissolved Organic Carbon in Sea Water" published in *Deep-Sea Research*, Vol. 16, pages 393-397 (1969), a technique is described for determining total organic carbon in a seawater sample by oxidizing dissolved organic matter in the sample with potassium peroxidisulfate as an oxidizing agent, using ultraviolet radiation to promote the oxidation. Carbon dioxide produced by oxidation of the organic matter is then measured for total carbon by conductometric means.

An article by P. D. Goulden and T. Brookbank entitled "Automated Determinations of Dissolved Organic Carbon in Lake Water" published in *Analytical Chemistry*, Vol. 47, pages 1943-1946 (1975) discusses a similar technique for determining total organic carbon in an aqueous sample. This article describes use of persulfate ion as an oxidizing agent in an ultraviolet-promoted oxidation reaction, and use of infrared detection means to measure total carbon in carbon dioxide produced by oxidation of the organic matter.

P. Wölfel and H. Sontheimer, in an article entitled "Ein neues Verfahren zur Bestimmung von organisch gebundenem Kohlenstoff im Wasser durch photochemische Oxidation" published in *Vom Wasser*, Vol. 43, pages 315-325 (1974), describes a technique for determining total organic carbon dissolved in an aqueous sample by exposing the sample to ultraviolet radiation from a low-pressure mercury vapor lamp immersed in the sample in order to oxidize organic matter in the sample to carbon dioxide, and then using infrared detection means to measure the carbon dioxide so produced. Immersion of the mercury vapor lamp in the sample enables the ultraviolet energy from the lamp to enter the sample directly after passing through the lamp envelope, thereby maximizing the energy available for oxidizing organic matter in the sample.

In U.S. Pat. No. 3,958,941 granted on an invention by M. Regan, a technique for determining total organic carbon in an aqueous sample is described in which air and water are circulated through an irradiation chamber having an ultraviolet lamp mounted therein. Separate air circulation and water circulation systems are provided, but both systems share a common flowline leading into the irradiation chamber. A sample to be analyzed for total carbon is injected into the common flowline, and is conveyed by the circulating water into the irradiation chamber wherein organic carbon in the sample is oxidized to carbon dioxide by radiation from the ultraviolet lamp. The air circulating through the irradiation chamber sparges carbon dioxide generated by the oxidation process from the chamber, and conveys the carbon dioxide to a conductometric device for determining total carbon.

Oxidation of dissolved carbonaceous matter in a liquid sample using ultraviolet radiation and an oxidizing agent to promote the oxidation process was known in the prior art. Nevertheless, attempts to automate the oxidation of carbonaceous matter in a plurality of discrete liquid samples in succession using ultraviolet radiation and an oxidizing agent encountered difficulties that were not overcome until the present invention.

When successive liquid samples are introduced into a reactor for oxidation of carbonaceous matter dissolved therein by an oxidizing agent and ultraviolet energy, complete oxidation of the carbonaceous matter in each successive sample cannot be assured unless the supply of oxidizing agent in the reactor is continuously replenished so as to provide sufficient oxidizing agent for each successive sample. Until the present invention, no technique was known for assuring that an adequate supply of oxidizing agent could be provided for each successive sample introduced into a reactor for total carbon analysis.

OBJECT OF THE INVENTION

It is an object of the present invention to provide method and apparatus for determining total carbon in each one of a plurality of discrete liquid samples in succession.

In accordance with the present invention, each liquid sample is introduced in succession into a reactor in which a source of ultraviolet radiation is disposed, and a continuous flow of a liquid containing an oxidizing agent is supplied to the reactor. The ultraviolet radiation causes oxidation of carbonaceous matter in each sample to carbon dioxide, and the carbon dioxide so formed is removed from the liquid in the reactor and is measured for total carbon. A uniformly adequate supply of oxidizing agent is continuously available in the reactor to insure complete oxidation of the carbonaceous matter in each liquid sample.

In one embodiment of the present invention, the liquid samples to be analyzed are introduced in succession into a flowline that carries the oxidizing agent into the reactor. In this embodiment, the flow rates of the oxidizing agent and of the liquid sample introduced into the flowline are additive; and any background carbon present in the oxidizing agent remains constant as each successive sample is conveyed into the reactor by the continuously flowing oxidizing agent.

In an alternative embodiment of the present invention, a quantity of carbon-free liquid is drawn from the reactor and returned to the reactor through a recirculation line; and the liquid samples to be analyzed are introduced in succession into the recirculation line for conveyance into the reactor by the carbon-free liquid circulating in the recirculation line.

In accordance with the present invention, carbon dioxide formed by oxidation of carbonaceous matter in each liquid sample is sparged from the reactor. The sparged carbon dioxide is then analyzed by conventional means for total carbon, thereby providing a measure of total carbon in the liquid sample.

DESCRIPTION OF THE DRAWING

FIG. 3 is a schematic representation of a portion of a system according to the present invention showing an alternative means from what is shown in FIG. 1 for determining total carbon in gas sparged from a reactor following oxidation of carbonaceous matter in the reactor.

DESCRIPTION OF PREFERRED EMBODIMENTS

Figure 1:
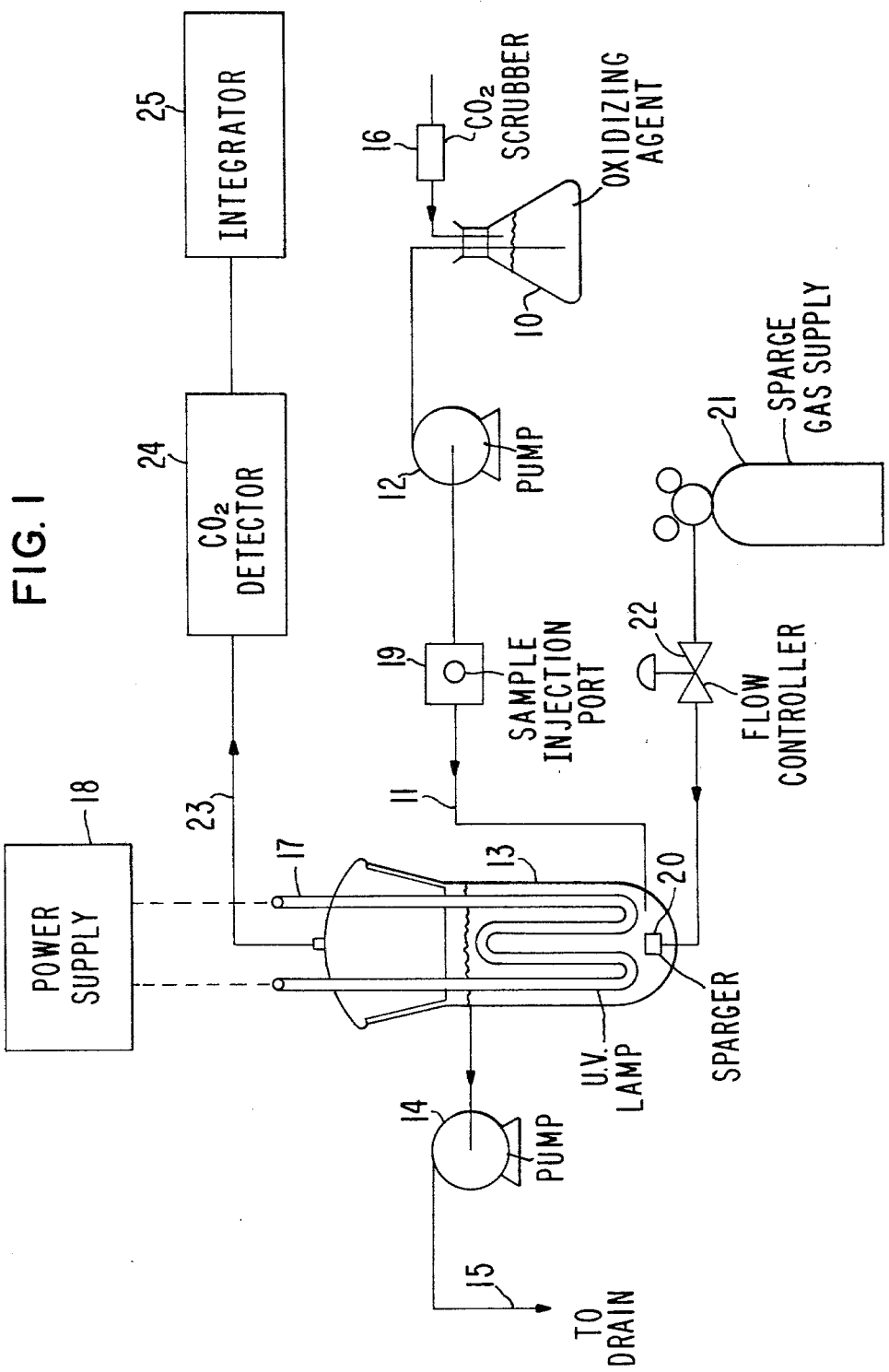
FIG. 1 is a schematic representation of a system according to the present invention for determining total carbon in each one of a plurality of discrete liquid samples.

In the system depicted schematically in FIG. 1, a continuous flow of liquid containing an oxidizing agent (in the usual case, a continuous flow of an oxidizing agent in aqueous solution) is pumped from a reservoir 10 via a flowline 11 by means of a pump 12 into a reactor 13. Although the volume of the reactor 13 is not critical to the practice of this invention, a typical volume for the reactor 13 is 0.1 liter. A pump 14 is provided to withdraw liquid from the reactor 13 via a flowline 15 to a drain at a rate sufficient to maintain a substantially constant liquid level in the reactor 13.

The oxidizing agent in the reservoir 10 preferably comprises persulfate ion $S_2O_8^{--}$, which is formed by dissolving a salt of persulfate in distilled or deionized water. The salt of persulfate most often used is potassium persulfate, but comparable oxidation efficiencies can be obtained using sodium persulfate or ammonium persulfate. An aqueous solution of hydrogen peroxide would also provide a suitable oxidizing agent, viz., hydroxy free radical .OH, for the practice of this invention. A carbon dioxide scrubber 16 is provided to remove carbon dioxide from air entering the reservoir 10, so that the liquid being pumped from the reservoir 10 is substantially carbon-free.

A mercury vapor lamp 17 having a quartz envelope is immersed in the liquid inside the reactor 13. The lamp 17 is powered by an electrical power supply 18 to emit electromagnetic radiation, which promotes oxidation of carbonaceous matter by the oxidizing agent in the reactor 13. Radiation emitted at the 2537-angstrom wavelength and at the 1849-angstrom wavelength is most effective in promoting oxidation of carbonaceous matter by the oxidizing agent. The 2537-angstrom wavelength is in the ultraviolet region of the electromagnetic spectrum, and the 1849-angstrom wavelength is often characterized by chemists as being in the vacuum-ultraviolet region.

The mercury vapor lamp 17 is of folded tubular configuration, and is designed to provide as much surface area as practicable in direct contact with the liquid in the reactor 13. In a preferred embodiment according to this invention, the reactor 13 is a generally cylindrical glass structure that can be filled to a selected level with liquid from the reservoir 10, which provides a constantly replenished supply of oxidizing agent to the reactor 13. The mercury vapor lamp 17 is a quartz tube folded to provide a plurality of elongate sections of substantially uniform cross-sectional area. The elongate sections of the lamp 17 are immersed in the liquid in the reactor 13, and extend parallel to each other and parallel to the cylindrical axis of the reactor 13.

In the embodiment shown in FIG. 1, each one of a plurality of liquid samples is introduced in succession (as by syringe injection) into the flowline 11 through a sample injection port 19. Each sample is then conveyed into the reactor 13 by the liquid flowing from the reservoir 10. Injection of the sample into the flowline 11 rather than directly into the reactor 13 eliminates the need to provide an injection port on the reactor 13, thereby enabling relatively fragile glass to be used in fabricating the reactor 13.

Inside the reactor 13, the ultraviolet radiation and the oxidizing agent cause oxidation of carbonaceous matter in the sample. Where the oxidizing agent comprises persulfate ion $S_2O_8^{--}$, the ultraviolet radiation $h\nu$ converts the persulfate ion to sulfate free radical $SO_4^-$. by the reaction $S_2O_8^{--} + h\nu \rightarrow 2SO_4^-$.. The ultraviolet radiation also excites the carbonaceous matter R to an excited state R* by the reaction $R + h\nu \rightarrow R^*$. The sulfate free radical then oxidizes the excited carbonaceous matter by the reaction $R^* + SO_4^-. + H_2O \rightarrow nCO_2 + \cdots$. Because a fresh supply of persulfate ion is continuously being delivered to the reactor 13, sufficient sulfate free radical is always available to cause complete oxidation of the carbonaceous matter in each succeeding sample that is injected into the flowline 11. Where the oxidizing agent comprises hydroxy free radical .OH, the .OH results from the dissociation of hydrogen peroxide due to ultraviolet radiation by the reaction $H_2O_2 + h\nu \rightarrow 2.OH$.

The carbon dioxide $CO_2$ formed by the oxidation process occurring in the reactor 13 is sparged from the reactor 13 by a carbon-free sparging gas that is introduced into the liquid near the bottom of the reactor 13 by a sparger 20, which is coupled to an external gas supply 21. The rate of introduction of the sparging gas into the reactor 13 can be controlled by a flow controller 22. It is important that the sparging gas flow rate through the liquid in the reactor 13 be constant if an infrared detection means is used to measure carbon dioxide produced by the oxidation process, as is discussed more fully hereinafter. Typically, an inert gas such as nitrogen is used as the sparging gas. However, a carbon-free gas containing molecular oxygen (e.g., air) could also be used as the sparging gas.

Referring to FIG. 1, gaseous products of the oxidation process occurring in the reactor 13 are sparged from the reactor 13 and passed via a flowline 23 to a conventional carbon dioxide detector 24. In particular applications where purgeable organic or other carbonaceous constituents might be sparged from the reactor 13 before being completely oxidized, the gas sparged from the reactor 13 could first be passed through an oxidation furnace in which all such carbonaceous constituents of the sparged gas would be pyrolyzed to carbon dioxide. The outflow from the oxidation furnace would then be passed to the carbon dioxide detector 24.

The carbon dioxide detector 24 is coupled to conventional means for determining total carbon in the sparged carbon dioxide. Conventional means suitable for determining total carbon in carbon dioxide include non-dispersive infrared detectors, coulometric titration cells, and conductometric measuring apparatus.

During the time interval when the carbonaceous matter in a given sample is being oxidized in the reactor 13, the carbon dioxide detector 24 generates a dynamic time-varying signal proportional to the amount of carbon dioxide detected. Over the complete time interval during which oxidation of the carbonaceous matter occurs, the signal generated by the carbon dioxide detector 24 exhibits a waveform that starts at a "zero" or baseline value when the sample is first injected, rises to a peak, and then falls back to the "zero" or baseline value as all of the carbonaceous matter in the sample is consumed by the oxidation process. Since the flow rate of liquid drawn from the reservoir 10 into the reactor 13 remains constant, the "zero" or baseline value of the signal generated by the carbon dioxide detector 24 uniformly accounts for any background carbon in the liquid drawn from the reservoir 10.

The signal generated by the carbon dioxide detector 24 can be integrated over the complete oxidation interval for each sample by conventional electronic integrator circuitry 25 to provide a measure of total carbon dioxide generated by oxidation of the sample in the reactor 13. Total carbon dioxide detected for each sample is a measure of total carbon present in the sample.

Automation of the sample injection technique illustrated in FIG. 1 would require mechanical apparatus and electronic instrumentation of major complexity. Therefore, an alternative technique has been developed for introducing liquid samples into the reactor 13 automatically. In the embodiment of the invention shown in FIG. 2, a pump 201 is provided for withdrawing a quantity of carbon-free liquid from the reactor 13 into an external recirculation line 202 through which the carbon-free liquid is circulated back to the reactor 13. The liquid samples are introduced in succession into the recirculation line 202 by means of a multi-position rotary valve 203, which is coupled to a sample loop 204 by conventional "zero dead volume" fittings. A six-position Teflon rotary valve of the type marketed by Rheodyne, Inc. of Berkeley, Calif. under the designation Type 50 is a suitable valve for the practice of this invention.

Figure 2:
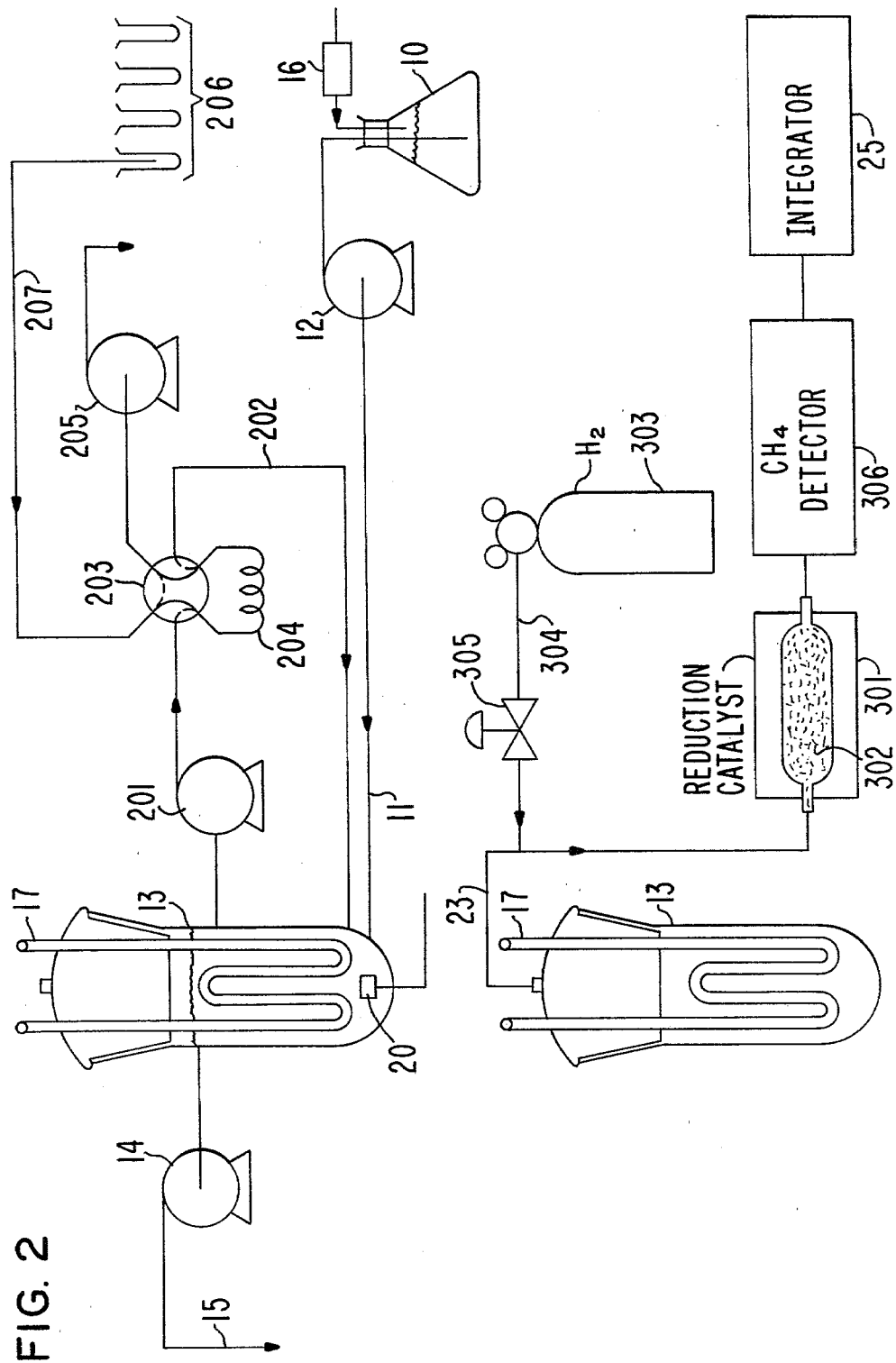
FIG. 2 is a schematic representation of a portion of a system according to the present invention showing an alternative means from what is shown in FIG. 1 for introducing liquid samples into a reactor.

As indicated schematically in FIG. 2, a pump 205 draws a liquid sample from a selected one of a plurality of sample containers 206 via a sample feedline 207 to the rotary valve 203. The valve 203 is internally configured to provide alternative flow paths for liquid passing therethrough, depending on the rotational position of a rotor portion with respect to a stator portion of the valve 203. Before a liquid sample is introduced into the recirculation line 202, the rotor portion of the valve 203 is positioned so that carbon-free liquid from the reactor 13 passes directly through the valve 203, while a sample from a selected one of the sample containers 206 passes from the valve 203 into the sample loop 204 and back to the valve for exit to a drain. In this way, the sample loop 204 is "loaded" with a precisely measured slug of sample liquid from the selected one of the containers 206.

After the sample loop 204 is "loaded" with a slug of sample liquid, the rotor portion of the valve 203 is rotated so that sample liquid from the selected one of the sample containers 206 thereafter passes directly through the valve 203 for exit to the drain, while carbon-free liquid from the reactor 13 is made to flow through the sample loop 204 in circulating back to the reactor 13. In this way, the slug of sample liquid in the sample loop 204 is displaced by an equal volume of carbon-free liquid, and the slug of sample liquid is conveyed into the reactor 13 by the circulating carbon-free liquid.

With samples of high carbon concentration, it is necessary to insure that sufficient oxidizing agent is available to enable complete oxidation of the carbonaceous matter in each sample. In the prior art, samples of high carbon concentration were usually diluted to a carbon concentration in the 50 ppb to 100 ppm range before being introduced into the reactor. However, with the sample introduction technique of the present invention, whether by syringe injection as in FIG. 1 or by rotary valve as in FIG. 2, dilution of a sample of high carbon concentration is unnecessary. Since each sample can be introduced into the reactor in as small a volume as desired, and since a fresh supply of oxidizing agent is continuously being supplied to the reactor 13, there is always sufficient oxidizing agent available to oxidize all carbonaceous matter in each sample. Using the present invention, total carbon has been determined for liquid samples having a carbon concentration as high as 1% (about 10,000 ppm).

Unlike the sample injection technique of FIG. 1 where the sample liquid is conveyed into the reactor 13 by a reagent-containing liquid whose flow rate remains constant, the valving technique of FIG. 2 does not utilize a constantly flowing liquid as the means for introducing the sample liquid into the reactor 13. According to the valving technique illustrated in FIG. 1, the flow rate of carbon-free liquid into the reactor 13 falls to zero when the slug of sample liquid sample enters the reactor. If a liquid sample were introduced into the flowline 11 rather than into a separate flowline such as the recirculation line 202, and if the carbon concentration of the liquid sample were less than the carbon concentration of the liquid containing the oxidizing agent (i.e., the liquid in the reservoir 10), then a negative total carbon measurement would be obtained for the sample. This problem of negative measurements is obviated, however, by using a carbon-free liquid as the transport means for conveying the liquid sample into the reactor 13. However, where the carbon concentration of the samples to be analyzed is so much higher than the carbon concentration of the liquid in the reservoir 10 that the carbon in the liquid in the reservoir 10 can be ignored, the valve 203 and associated sample loop 204 could be placed in the flowline 11 and the recirculation line 202 would not be needed.

An automated total carbon determination system utilizing the valving technique illustrated in FIG. 2 can be programmed by conventional methods to draw liquid from each one of the sample containers 206 in succession, with the sample loop 204 being "loaded" with a slug of sample liquid drawn from a given one of the containers 206 as soon as the carbon dioxide detector 24 indicates that all carbonaceous matter in a slug drawn from the immediately preceding container of sample liquid has been completely oxidized. In this way, each successive slug of sample liquid can be introduced into the reactor 13 as soon as the liquid in the reactor is free of carbon from the preceding sample liquid slug, rather than at some arbitrary time interval following introduction of the preceding sample liquid slug into the reactor 13.

In an alternative embodiment shown in FIG. 3, the gas sparged from the reactor 13 following oxidation of carbonaceous matter in a liquid sample, instead of being passed to a carbon dioxided detector as in FIG. 1, is passed to a reduction chamber 301 containing a catalyst 302 such as nickel or rhodium that converts carbon dioxide and other carbonaceous gases to methane in the presence of hydrogen gas. A source 303 of hydrogen gas is coupled to the gas outlet flowline 23 of the reactor 13 by a conduit 304 in which a regulator valve 305 is provided. Carbon dioxide is converted to methane in the reduction chamber 301 by the reaction $CO_2 + 4H_2 \rightarrow CH_4 + 2H_2O$. The methane produced in the reduction chamber 301 is then passed to a methane detector 306, which comprises means for quantitatively measuring total carbon in methane. A suitable methane detector 306 is e.g., a flame ionization detector.

The present invention has been described above in terms of particular techniques for introducing liquid samples into a reactor, and for measuring total carbon in the gas evolved from oxidation in the reactor of carbonaceous matter in each liquid sample. Other particular techniques for implementing the present invention could be devised by workers skilled in the art, and yet be within the scope of the present invention. The above description, therefore, is not to be construed in limitation of the invention but rather is to be understood as illustrative. The scope of the invention is defined by the following claims and their equivalents.

What is claimed is:

1. Apparatus for determining total carbon in a liquid sample comprising: a reactor, a flowline leading into said reactor, means defining a source of a liquid containing an oxidizing agent connected to and communicating with said flowline, means for maintaining a continuous flow of said liquid containing said oxidizing agent into said reactor via said flowline, means for introducing a liquid sample into said reactor, a source of electromagnetic radiation positioned inside said reactor so as to be immersed in said liquid containing said oxidizing agent, said electromagnetic radiation causing oxidation of carbonaceous matter in each sample, means for causing gas produced by oxidation of said carbonaceous matter in each sample to be removed from said reactor, means operatively connected to said last-mentioned removal means for measuring total carbon in said gas, said means for introducing said liquid sample into said reactor comprising means for continuously withdrawing liquid from said reactor, means for introducing a selected quantity of the liquid sample into the liquid removed from the reactor, and means separate from said flowline for continuously recirculating said liquid continuously removed from the reactor together with any selected quantity of sample liquid therein back to the reactor.

2. The apparatus according to claim 1 wherein said means for introducing a selected quantity of the liquid sample into said removed liquid comprises a sample loop, a sample input line into which the liquid sample is introduced, and valve means operatively connected between said means for continuously removing the liquid from the reactor, said sample loop, said sample input line and said means for continuously recirculating the removed liquid back to the reactor, said valve means including means for first directing liquid sample from said sample input line into said sample loop to fill the sample loop with the liquid sample and for thereafter directing the removed liquid from said means for continuously removing liquid from the reactor through the sample loop into said means for continuously recirculating the removed liquid back to the reactor.

3. The apparatus according to claim 2 further including a drainage line, said valve means including a stator having six ports, with a first port being connected to said means for continuously removing liquid from the reactor, a second port connected to said sample input line, third and fourth ports connected to the inlet and outlet ends of said sample loop, a fifth port connected to said means for continuously recirculating removed liquid back to said reactor and a sixth port connected to said drainage line, said valve means further including a rotor having internal passageways which, when in a first position relative to the stator, directs sample liquid from said sample input line into said sample loop and from said sample loop into said drainage line and which, when in a second position, directs liquid removed from the reactor into the sample loop previously filled while the rotor was in said first position and for directing the liquid from the sample loop into said means for recirculating the liquid back to the reactor.

4. Apparatus for determining total carbon in a liquid sample comprising: a reactor, a flowline leading into said reactor, means defining a source of a liquid containing an oxidizing agent connected to and communicating with said flowline, means for maintaining a continuous flow of said liquid containing said oxidizing agent into said reactor via said flowline, means for introducing said samples into said reactor, a source of electromagnetic radiation positioned inside said reactor so as to be immersed in said liquid containing said oxidizing agent, said electromagnetic radiation causing oxidation of carbonaceous matter in each sample, means for causing gas produced by oxidation of said carbonaceous matter in each sample to be removed from said reactor, means operatively connected to said last-mentioned removal means for measuring total carbon in said gas, said means for introducing said samples into said reactor comprising means for continuously withdrawing liquid from said reactor, means for introducing a selected quantity of the sample into the liquid removed from the reactor, and means for continuously recirculating the liquid removed from the reactor together with the selected quantity of sample back to the reactor, said means for introducing a selected quantity of sample into said removed liquid comprising a sample loop, a sample input line into which the sample is introduced, and valve means operatively connected between said means for continuously removing the liquid from the reactor, said sample loop, said sample input line and said means for continuously recirculating the removed liquid back to the reactor, said valve means including means for first directing liquid sample from said sample input line into said sample loop to fill the sample loop and for thereafter directing the removed liquid from said means for continuously removing liquid from the reactor through the sample loop into said means for continuously recirculating the removed liquid back to the reactor.

5. The apparatus according to claim 4 further including a drainage line, said valve means including a stator having six ports, with a first port being connected to said means for continuously removing liquid from the reactor, a second port connected to the inlet and outlet ends of said sample loop, a fifth port connected to said means for continuously recirculating removed liquid back to said reactor and a sixth port connected to said drainage line, said valve means further including a rotor having internal passageways which, when in a first position relative to the stator directs liquid sample from within said sample input line into said sample loop and from said sample loop into said drainage line and which, when in a second position, directs liquid removed from the reactor into the sample loop previously filled while the rotor was in said first position and for directing the liquid from the sample loop into said means for recirculating the liquid back to the reactor.

* * * * *